United States Patent
Schindly et al.

(10) Patent No.: US 6,749,807 B1
(45) Date of Patent: *Jun. 15, 2004

(54) FLOW THROUGH CHEMICAL INDICATOR FOR MEASUREMENT OF ACTIVE BIOCIDAL AGENTS IN A SINGLE USE PACKAGE

(75) Inventors: Brian E. Schindly, Mentor, OH (US); Christopher M. Fricker, Concord, OH (US); George E. Grignol, Fairview, PA (US)

(73) Assignee: Steris Corporation, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,497

(22) Filed: May 19, 1999

(51) Int. Cl.$^7$ .............. B01L 3/00; B01D 11/02; G01N 31/00; G01D 21/00; B65D 85/04
(52) U.S. Cl. .............. 422/28; 422/1; 422/102; 422/263; 422/266; 422/277; 422/278; 422/292; 436/1; 436/50; 436/55; 116/206; 206/59.1
(58) Field of Search .............. 422/1, 28, 263, 422/264, 266, 275, 277, 278, 292, 55, 56, 57, 58, 61, 62, 102; 436/1, 50, 55; 116/206; 206/59.1

(56) References Cited

U.S. PATENT DOCUMENTS

| | | | |
|---|---|---|---|
| 4,206,844 A | * | 6/1980 | Thukamoto et al. ......... 422/86 |
| 4,362,645 A | * | 12/1982 | Hof et al. ................ 252/408.1 |
| 4,407,960 A | * | 10/1983 | Tratnyek .................... 436/1 |
| 4,731,222 A | * | 3/1988 | Kralovic et al. ............. 422/37 |
| 5,037,623 A | * | 8/1991 | Schneider et al. ........... 422/292 |
| 5,077,008 A | | 12/1991 | Kralovic et al. ............. 422/37 |
| 5,116,575 A | | 5/1992 | Badertscher et al. .......... 422/28 |
| 5,209,909 A | * | 5/1993 | Siegel et al. ................ 422/292 |
| 5,217,698 A | | 6/1993 | Siegel et al. ................ 422/295 |
| 5,225,160 A | | 7/1993 | Sanford et al. .............. 422/28 |
| 5,350,563 A | | 9/1994 | Kralovic et al. ............. 422/28 |
| 5,403,549 A | * | 4/1995 | McNeil et al. ............... 422/29 |
| 5,417,676 A | * | 5/1995 | Watanabe et al. ............ 604/317 |
| 5,439,654 A | | 8/1995 | Kochte ...................... 422/292 |
| 5,489,281 A | * | 2/1996 | Watanabe et al. ............ 604/317 |
| 5,518,927 A | * | 5/1996 | Malchesky et al. ........... 436/1 |
| 5,552,115 A | | 9/1996 | Malchesky .................. 422/28 |
| 5,662,866 A | * | 9/1997 | Siegel et al. ................ 422/29 |
| 5,942,438 A | * | 8/1999 | Antonoplos et al. .......... 436/1 |
| 5,997,814 A | * | 12/1999 | Minerovic et al. ........... 422/29 |
| 6,287,518 B1 | * | 9/2001 | Ignacio et al. .............. 422/86 |

* cited by examiner

*Primary Examiner*—Robert J. Warden, Sr.
*Assistant Examiner*—Monzer R. Chorbaji
(74) *Attorney, Agent, or Firm*—Fay, Sharpe, Fagan, Minich & McKee, LLP (57) ABSTRACT

A single-use cartridge C contains a dose of a concentrated decontaminant for providing a decontaminant solution upon mixing with water. The cartridge is inserted into the well (16) of a decontamination system (A). Fresh water and then the decontaminant solution are recirculated through the well during a decontamination cycle. The cartridge includes a porous region (42), through which the decontaminant solution flows. Impregnated in the porous region is a chemical indicator (44), such as crystal violet, which gradually changes color on exposure to the decontaminant. The indicator provides a semi-quantitative indication of the integrated level of the decontaminant in the solution over time for determining whether an acceptable level of the decontaminant was present for decontamination. A preferred embodiment of the cartridge C includes nested inner and outer water-penetrable cups (50,150,70,170) for holding first and second reagents. The two cups are sealed together adjacent upper open ends (56,92,156,192). A porous top cover (94, 194) is sealed to the inner cup adjacent the inner cup open end (92, 192) to complete the cartridge. The two reagents react with water flowing through the cartridge to form the decontaminant solution. The chemical indicator is printed on the top cover so that it is exposed to the decontaminant solution as it is recirculated through the cartridge.

23 Claims, 6 Drawing Sheets

FLOW THROUGH CHEMICAL INDICATOR FOR MEASUREMENT OF ACTIVE BIOCIDAL AGENTS IN A SINGLE USE PACKAGE

BACKGROUND OF THE INVENTION

The present invention relates to the sterilization and disinfection arts. It finds particular application in conjunction with the evaluation of the concentration of peracetic acid in a sterilization or disinfection system obtained from a single use package of a concentrated decontaminant composition and will be described with particular reference thereto. It should be appreciated, however, that the invention is also applicable to other liquid sterilization and disinfection processes where the sterilant or disinfectant is effective above a minimum effective concentration, such as liquid hydrogen peroxide or sodium hypochlorite sterilization or disinfection systems.

Disinfection connotes the absence of pathogenic life forms. Sterilization connotes the absence of all life forms, whether pathogenic or not. The term decontamination is used herein to connote sterilization, disinfection or other antimicrobial treatments.

Until recently, medical equipment and instruments were often decontaminated in a steam autoclave. Autoclaves kill life forms with a combination of high temperature and pressure. However, steam autoclaves have several drawbacks. The high temperature pressure vessels are often bulky and heavy. The high temperature and pressure tend to curtail the useful life of endoscopes, rubber and plastic devices, lenses, and portions of devices made of polymeric materials and the like. Moreover, a typical autoclave decontaminating and cool down cycle is sufficiently long that multiple sets of the medical instruments are commonly required.

Liquid decontamination systems have been developed for equipment which could not withstand the high temperatures of steam decontamination. Commonly, a technician mixes a liquid disinfectant composition immediately prior to use and manually immerses the items to be decontaminated. The high degree of manual labor introduces numerous uncontrolled and unreported variables into the process. There are quality assurance problems with the weakening of the decontaminant chemicals due to aging on the shelf, and technician errors in the mixing of decontaminant, control of immersion times, rinsing of residue, exposure to the ambient atmosphere after the rinsing step, and the like. On occasion, powdered reagents are carried away from the mixing region and deposited in undesired locations before they dissolve or react. When such systems are used for decontaminating medical instruments, undissolved reagent particles remaining on the medical instruments after a decontamination process are considered undesirable.

Recently, integrated decontamination systems, such as peracetic acid decontamination systems, have been developed which provide a premeasured dose of a decontaminant in solution. Items to be sterilized are inserted into a receiving tray of a sterilization system and a cartridge of concentrated decontaminant inserted into a well. As water flows through the system, the decontaminant is diluted and carried to the receiving tray. At the end of a decontamination cycle, the decontaminant solution is disposed of and a fresh cartridge of the concentrated decontaminant inserted into the system for the next cycle.

U.S. Pat. No. 5,662,866 to Siegel, et al. discloses a two-compartment cup for use in such a system, which holds powdered sterilant reagent components. An outer cup holds a first reagent while an inner cup, disposed within the outer cup, holds a second reagent. Peripheral walls of inner and outer cups are affixed together at their open ends at flanges. A permeable sheet is affixed to the inner cup portion flange for sealing both cups and for allowing venting of gases from the inner cup during storage. The outer cup is closed at its base by a first detachable base and the inner cup is similarly closed by a second detachable base. In use, the two bases are opened to allow mixing of the two reagents. The two-compartment cup provides a reproducible, pre-measured dose of reagents, while also facilitating handling and shipping of the reagents.

It is trusted that the decontamination system will be at or above the minimum effective concentration of the decontaminant for a predetermined period, so that effective decontamination is obtained. However, differences in ambient temperature, the quantity of items to be disinfected or sterilized and the level of contamination on the items can, nevertheless, lead to variations in how well the decontaminant concentration is maintained over the period of the decontamination cycle. In addition, storage conditions sometimes lead to degradation of peracetic acid precursors before use. Other factors, such as poor instrument cleaning or water quality may also affect decontaminant concentration. For medical instruments in particular, therefore, an additional assurance of satisfactory peracetic acid concentration is desired.

Dippable, chemically-treated papers are available for checking that the peracetic acid concentration in the sterilization system reached a minimum acceptable level for sterilizing or disinfecting. A chemically-treated paper strip is typically inserted into the decontamination system and evaluated at the end of the cycle for a color change, or other indication that the level of the decontaminant has been satisfactory. However, such strips are often omitted from the sterilization system, lost, or remain in the system for several cycles, and thus they are not a reliable record of whether the correct level of decontaminant was obtained in each cycle.

The present invention provides for a new and improved decontaminant package and indicator system and method of use which overcomes the above-referenced drawbacks and others.

SUMMARY OF THE INVENTION

In accordance with one aspect of the present invention, a single-use package for holding and selectively releasing a powdered composition is provided. The composition forms a solution of an anti-microbial decontaminant when mixed with water. The package includes a porous portion which is impermeable to the powdered composition but is permeable to water and to the solution. An indicator on the porous portion exhibits a detectable change on exposure to the decontaminant in the solution.

In accordance with another aspect of the present invention, a package for releasing an antimicrobial composition into a flowing liquid is provided. The package includes a side wall having a first opening at a first end and a second opening at a second end such that the liquid flows through the first opening into the package and out through the second opening. A layer of porous material spans one of the first and second openings such that the liquid flows through the porous material layer. An antimicrobial source is disposed within the package for releasing the antimicrobial composition into the flowing liquid to form an antimicrobial solution. An indicator on the porous material layer changes color in response to contact with the antimicrobial solution. The degree of color change varies in accordance with (i) the concentration of an antimicrobial agent in the solution contacting the indicator, and (ii) the duration that the solution contacts the indicator. The degree of color change of the indicator is indicative of duration of contact and the concentration of the antimicrobial agent in the contacting solution.

In accordance with yet another aspect of the present invention, a method includes flowing water through a cartridge containing a composition to form a decontaminant solution from the composition and the water. The cartridge includes a porous region impregnated with an indicator. The indicator exhibiting a detectable change when contacted with a decontaminant solution for a period of time and at a concentration of a decontaminant in the solution sufficient to effect decontamination of items. The method further includes circulating the decontaminant solution in a fluid flow path comprising a microbial decontamination chamber, in which the items to be decontaminated are positioned, and the porous region, and examining the indicator for the detectable change.

One advantage of the present invention is that it provides a rapid method of indicating that adequate levels of a decontaminant in a decontamination cycle were maintained.

Another advantage of the present invention is that it ensures that the level of decontaminant is evaluated in every decontamination cycle.

Yet another advantage of the present invention is that it provides a record of decontaminant levels which may be stored with other records of the decontamination cycle.

A further advantage of the present invention is that it provides a clear yes-or-no indication of whether a minimum effective concentration of peracetic acid was present during the entire cycle.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
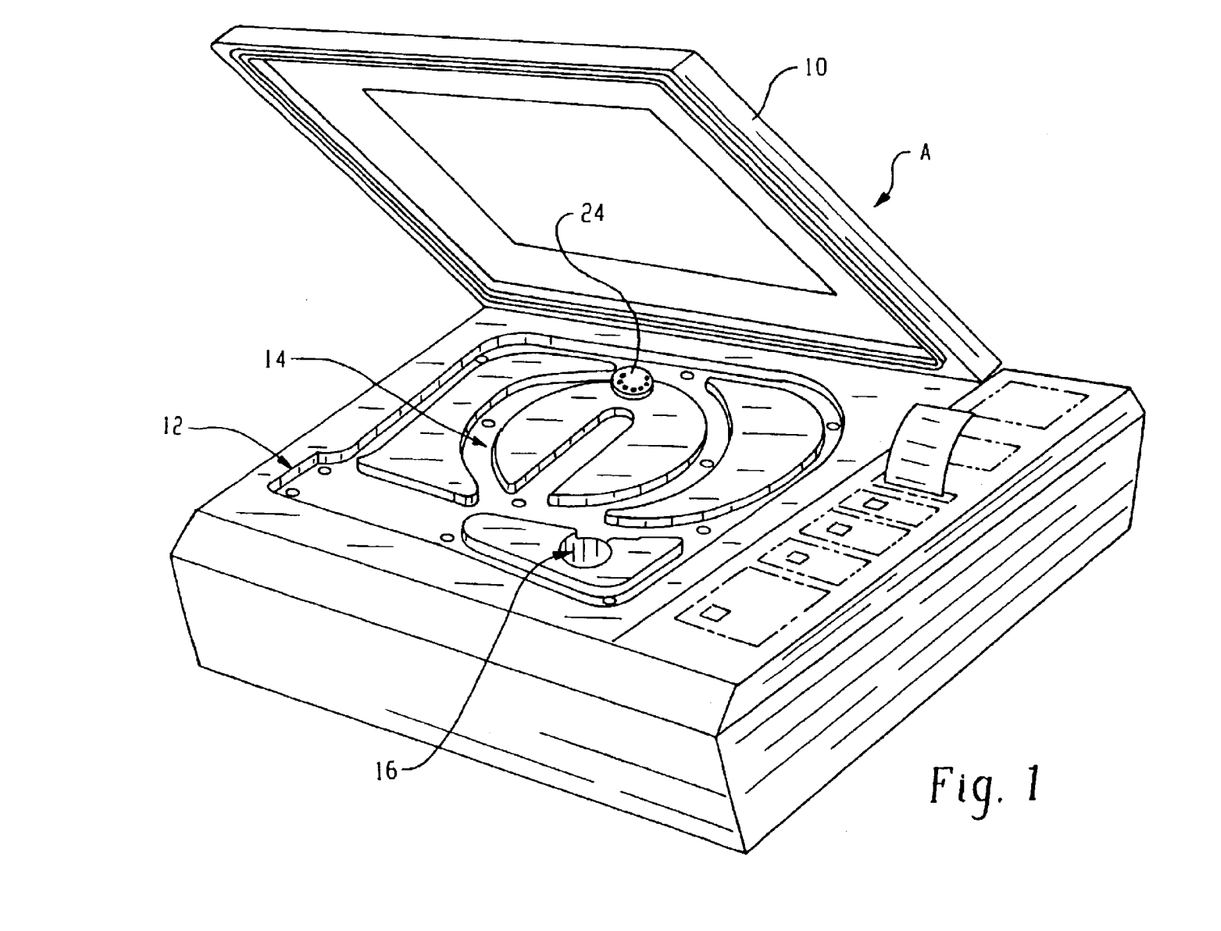
FIG. 1 is an exterior view of a decontamination unit according to the present invention.
Figure 2:
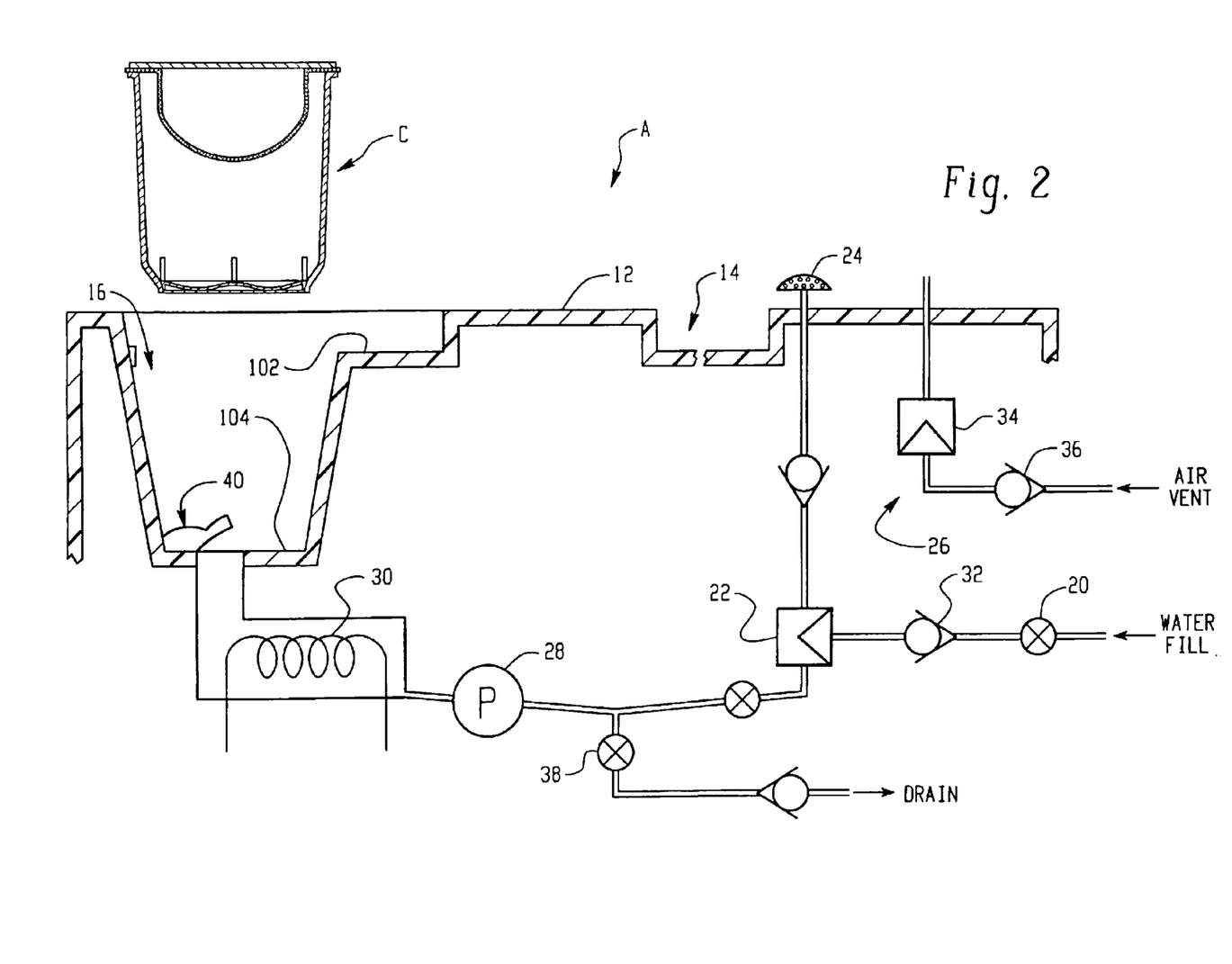
FIG. 2 is a plumbing diagram of the decontamination unit of FIG. 1 including a cross-sectional view of a reagent cartridge receiving well and one embodiment of a two-compartment reagent package according to the present invention.

With reference to FIGS. 1 and 2, a microbial decontamination apparatus A is configured to sit on a counter top or other convenient work surface. A door or lid 10 is manually openable to provide access to a tray 12 which defines a receiving region 14 for receiving items to be microbially decontaminated. In the illustrated embodiment, the tray 12 is configured to receive endoscopes or other long, coilable items. Other trays with item receiving regions of different configurations for receiving the items themselves or item holding containers are also contemplated. A well 16 receives a unit dose of reagents for forming a sterilant, disinfectant, or other microbial decontaminating solution.

With particular reference to FIG. 2, a decontaminant containing package, cup, or cartridge C is inserted into the well 16. Once the items are loaded into the tray and the decontaminant carrying cartridge C is inserted into the well 16, the lid 10 is closed and latched. A fill valve 20 passes water through a microbe removing filter 22 in flow paths of a fluid circulating system. The microbe removing filter 22 provides a source of sterile water by passing water and blocking the passage of all particles the size of microbes and larger. The incoming water which has been sterilized by the filter 22 passes through a spray or distribution nozzle 24 and fills the item receiving region 14 in the tray 12. As additional water is received, it flows into the well 16 dissolving the decontaminant in the cartridge C, and forming an antimicrobial solution. Filling is continued until all air is forced through an air system 26 and an entire interior volume is filled with the sterile water.

After the fill valve 20 is closed, a pump 28 circulates the fluid through a heater 30, the item receiving region 14 of the tray 12, and the well 16. The pump also forces the antimicrobial solution through the filter 22 to a check valve 32 sterilizing the filter. Further, the pump forces the antimicrobial solution through another microbe filter 34 in the air system 26 to a check valve 36. After the anti-microbial solution has been brought up to temperature and circulated for a selected duration, a drain valve 38 is opened, allowing the solution to drain. Air is drawn through the microbe filter 34 such that sterile air replaces the fluid within the system. Thereafter, the drain valve is closed and the fill valve 20 opened again to fill the system with a sterile rinse fluid. It will be noted, that because the pump 28 circulated the anti-microbial solution over all surfaces of the flow paths including all surfaces leading from the sterile rinse source 22, the rinse cannot bring microbial contaminants into the item receiving region 14.

A lower opener projection or member 40 is optionally disposed at the bottom of the well for engaging a lower surface of the cartridge C as it is inserted into the well, thereby opening the cartridge.

Although FIGS. 1 and 2 show a preferred embodiment of a decontamination system A for use with a disposable, single use cartridge C, other embodiments of the decontamination system are also contemplated. An important feature of a suitable decontamination system is that it recirculates the decontaminant solution through the cartridge, or otherwise contacts the cartridge with the decontaminant solution, during a decontamination cycle.

Figure 3:
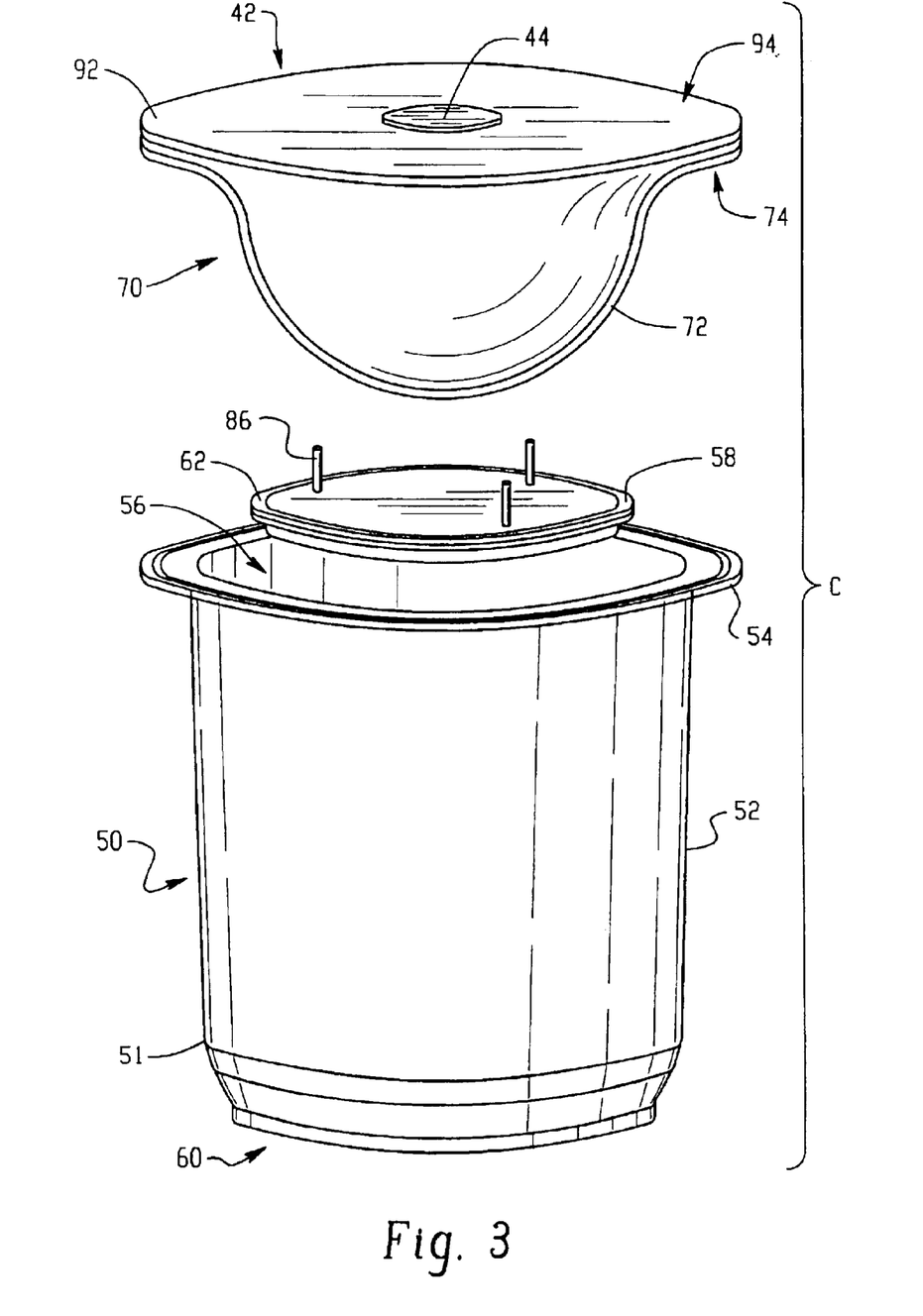
FIG. 3 is an exploded perspective view of a first embodiment of the two compartment package in accordance with the present invention.
Figure 4:
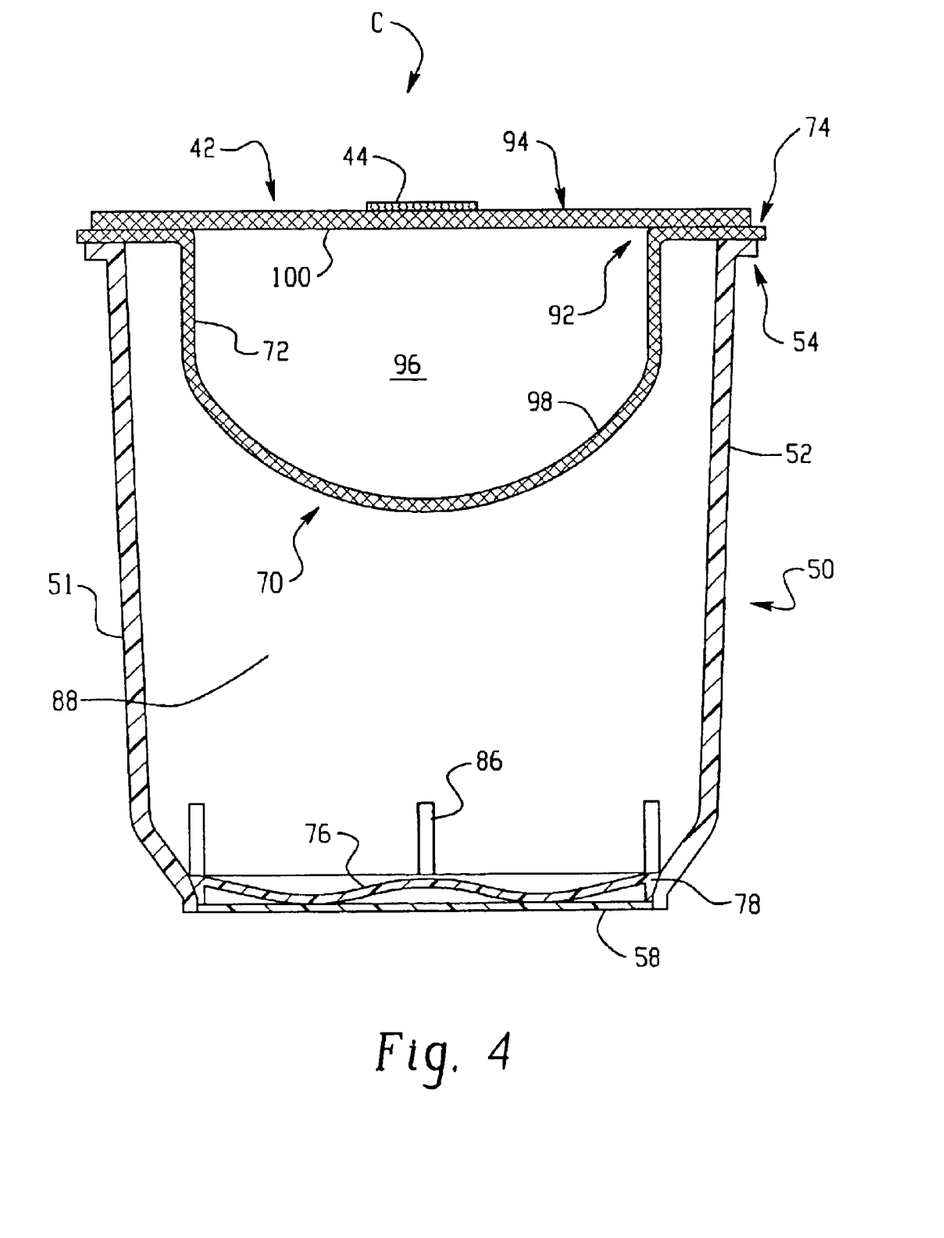
FIG. 4 is a side sectional view of the two-compartment package of FIG. 3.
Figure 5:
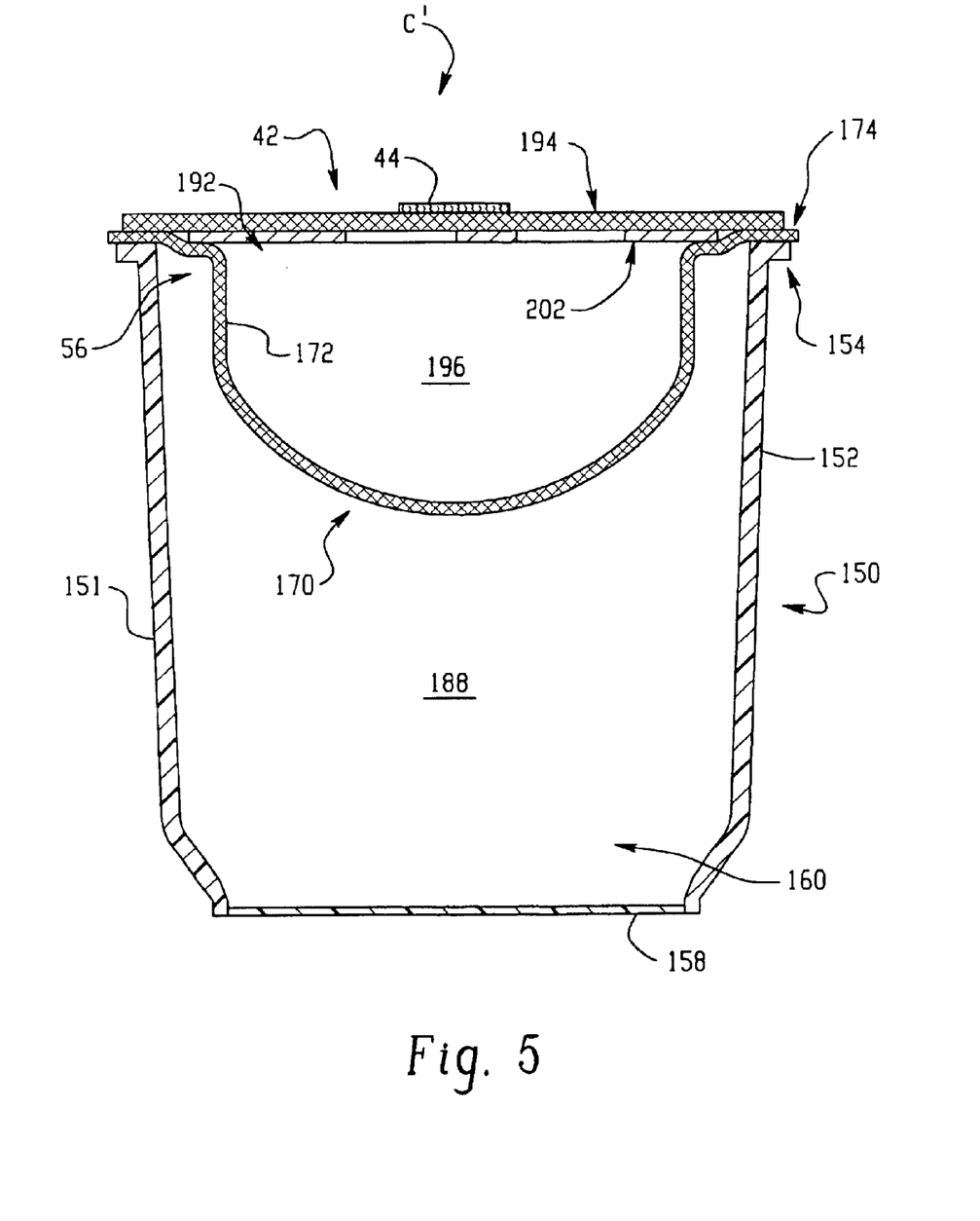
FIG. 5 is an alternate embodiment of the package of FIGS. 3 and 4.

With reference also to FIGS. 3–5, the single-use cartridge C contains a dose of a concentrated decontaminant for providing a decontaminant solution upon mixing with water. Specifically, the cartridge C holds a soluble decontaminant, in dry form, or two or more powdered, crystalline, or other non-liquid reagents which, when diluted with water, react to form an anti-microbial solution. The cartridge includes a porous portion 42 through which the anti-microbial solution passes during a decontamination cycle. A chemical indicator 44 for the decontaminant is printed on, or otherwise affixed to the porous portion 42 for detecting the decontaminant in the anti-microbial solution flowing through the porous portion. Since a fresh cartridge C is used with each cycle, this guarantees that a new chemical indicator is used for each cycle. Preferably, the porous portion 42 is a readily observable portion of the cartridge C, such as a lid of the cartridge, so that an operator's attention is drawn to the indicator when removing the cartridge from the decontamination system at the end of the cycle.

A variety of configurations for the decontaminant package cartridge C are contemplated. With reference to FIGS. 3 and 4, a first embodiment of the cartridge C includes a first, outer cup, or cup portion 50. The outer cup is constructed of a light weight, rigid polymeric material. The outer cup 50 includes a peripheral wall 51. The peripheral wall has a cylindrical side 52, that has a flange 54 at a first, open upper end 56 thereof, and a closure, such as a detachable base wall 58. The base wall is impermeable to a reagent disposed in the outer cup and closes a second, opposite end 60 of the side 52. The detachable base wall 58 is secured to the second end by being snapped in and held by a lip and groove, friction engagement, a breakable seal, or the like. When force or pressure is applied to the detachable base wall from beneath the outer cup 50 by the lower opener member 40, the detachable base wall 58 detaches. An enlarged flange 62, or the like, retains the base wall in the interior of the outer cup by making the diameter of the base wall larger than the opening at the second end.

A second or inner cup 70 is received in the outer cup 50. The inner cup has a generally thermally molded, hemispherical peripheral wall 72 that has an integrally molded flange 74. Alternatively, the inner cup peripheral wall is cone shaped, cylindrically shaped, or the like.

With particular reference to FIG. 4, the detachable base wall 58 has a domed central region 76. The domed central region is surrounded by a vertical wall 78 that frictionally engages the cylindrical side 52 of the outer cup. As force is applied to the domed central region, it flexes. The flexing urges the attached vertical wall away from the cylindrical side of the outer cup producing the frictional engagement and facilitating its release. Optionally, a plurality of legs 86 or other spaced projections are provided on the base wall for maintaining a spaced distance between the outer and inner cups upon release of the outer cup base wall 58.

Preferably, the inner cup peripheral wall 72 is about half the height of the outer cup peripheral wall 51 such that a first reagent chamber 88 is defined therebetween. The inner cup 70 is sealed at a first or top end 92 by a top cover 94 which provides the porous portion 42. Together, the inner cup 70 and top cover 94 define a second reagent receiving chamber 96.

The peripheral wall 72 of the inner cup 70 and top cover 94 are preferably formed from a material that is impermeable to the dry reagent contained within the inner and outer cups, yet is permeable to water and to dissolved reagents. Alternatively the peripheral wall 72 includes a region 98 that is formed from a material which is impermeable to powdered reagents but which is permeable to water and to dissolved reagents. A similar region 100 is optionally included in the top cover, which defines the porous portion 42. Any particles of reagent in the inner cup 70 that are not dissolved are therefore trapped within the cartridge. Dissolved reagents pass through the material and are transported to the items to be sterilized.

The choice of material for the top cover 94 and inner cup wall 72 depends on the particle size of the reagents. For reagents having a particle size of about 50 microns, a non-woven polypropylene web or felt keeps the dry reagents from penetrating the material, while allowing the water and dissolved reagents to pass freely through the inner cup 70 and top cover 94. When the material is a polypropylene web, the top cover is readily sealed to the inner cup by ultrasonically welding or other heat sealing the flange of the inner cup to the top cover. Other suitable filter materials include woven polypropylene, woven or nonwoven polyethylene, nylon, and rayon, rigid porous media, such as POREX™ expanded plastic, or other porous plastic, fabric, felt, mesh, and analogous materials.

The material for the inner cup and top cover is preferably free of additives, such as binders or surfactants, that could be dissolved in the water and contaminate the items to be decontaminated. The material is also preferably lint free, so that small particles of the material do not come away from the inner cup and become trapped within items to be decontaminated. Further, the material preferably has a fairly high tensile strength and does not disintegrate when it is subjected to a fairly high pressure of water. The material is also preferably unreactive toward the reagents and other additives used in the decontamination unit. An extruded spun-bonded polypropylene web having an absolute pore size of under 50 microns, and preferably around 10 microns, is a preferred material because it is virtually lint-free. It also has a high tensile strength, even when under a moderately high water pressure. The material is preferably molded to the shape of the inner cup 70 from a single sheet of the polypropylene web. Alternatively, the flange 74 is formed from a separate material which is then welded to the remainder of the outer cup. The porous nature of the inner cup and top cover 94 allows gases formed from the reagents during transit to out gas from the cartridge C.

Optionally, the material also acts as a filter for filtering particles, such as microorganisms and dirt, from the anti-microbial solution passing through the cartridge.

With continuing reference to FIGS. 3 and 4, the inner and outer cups are configured such that the flanges 54, 74 abut and are sealed together. Appropriate sealing means for the flanges include heat welding, adhesive bonding, solvent welding, ultrasonic welding, or the like. When the inner cup and top cover are constructed of a spun-bonded polypropylene and the outer cup is also formed from polypropylene, the top cover, inner cup, and outer cups are preferably ultrasonically or heat welded together at the same time, thereby forming a seal which extends from the top cover and through the flange on the inner cup to the flange on the outer cup.

In an alternative version of this embodiment (not shown), the inner cup is constructed in a similar manner to the outer cup 50. Specifically, the inner cup includes a peripheral wall with a cylindrical side of slightly smaller cross sectional diameter than that of the outer cup cylindrical side 52. A detachable base, similar to the outer cup base 58, closes off a lower open end of the inner cup side, while an upper open end of the inner cup side defines a flange for sealing to the outer cup flange 54. The inner cup base of this version is detached by the spaced projections 86 when the outer cup base 58 is detached. A top cover 94, of the type previously described, is sealed to the inner cup flange in the manner described above.

To assemble the cartridge C, the base 58 is first installed in the outer cup 50. The first reagent, such as a dry mixture of sodium perborate, corrosion inhibitors, pH buffers, detergents and wetting agents is then disposed within the outer cup. The inner cup 70 is then placed within the outer cup with the flange 74 of the inner cup resting on the flange 54 of the outer cup. The second reagent, preferably an acetyl donor, such as acetylsalicylic acid, is disposed within the inner cup and the top cover 94 disposed so that it rests on the flange of the inner cup. The top cover, inner cup and outer cup are then sealed together at the flanges of the inner and outer cup. Specifically, the inner cup flange 74 is pressed against the outer cup flange 54 for ultrasonic or heat welding. Preferably, an outer edge of the top cover 78 is sealed to the inner cup flange 74 in the same welding operation. Under heat or ultrasonic vibration, the plastic melts and flows into the fibers or into the voids of other porous filter materials, forming a unitary seal. Alternatively, other methods of sealing, such as gluing, fusion bonding, clamping with a clamping ring, or the like, replace the heat or ultrasonic welding as a means of joining the various components. Thus, the first reagent is sealed within the outer cup, while the second reagent is sealed within the inner cup.

The cartridge C is configured so that substantially all the water, and subsequently the decontaminant solution, entering the well 16 of the decontamination system A is forced through the top cover 94, and into contact with the indicator 44. In one preferred embodiment, the flange 54 of the outer cup is clamped into sealing contact with a rim 102 of the well 16 when the lid 10 of the decontamination system is closed. Alternatively, the closing of the lid brings the lower end 60 of the outer cup into sealing engagement with a base 104 of the well.

With reference to FIG. 5, an alternate embodiment of the two compartment package C' includes a first, or outer cup portion 150. The outer cup 150 is constructed of a light weight, rigid polymeric material. The outer cup 150 includes a peripheral wall 151 with a cylindrical side 152 that has a flange 154 at a first, open end 156 thereof. A fluid-permeable base, or porous filter 158 covers a second, opposite, or lower end 160 of the cylindrical side 152. The porous filter 158 is ultrasonically welded or otherwise adhered to the side 152, thereby covering the lower end 160 of the outer cup. The outer cup is then filled with reagent components, such as sodium perborate, corrosion inhibitors, pH buffers, detergents and wetting agents. The filter 158 is preferably formed from a material that is impermeable to the dry reagents that are contained within the outer cup portion, yet is permeable to water with dissolved reagents.

A second, or inner cup 170, similar to the inner cup 70 of the first embodiment, is received in the outer cup 150. The inner cup includes a thermally molded, peripheral wall 172 which defines a generally hemispherical cup with an integrally molded flange 174. Alternatively, the inner cup peripheral wall is cone or cylindrically shaped. A first reagent-receiving chamber is 188 defined between the outer cup 150 and the inner cup peripheral wall 172. The inner cup 170 is filled with a second reagent component, preferably an acetyl donor such as acetylsalicylic acid.

The peripheral wall 172 of the inner cup 170 is formed, like the inner cup 70 of the first embodiment, from a filter material that is impermeable to the dry reagents contained within the inner and outer cups, yet is permeable to water and to the dissolved reagents. A top opening 192 of the inner cup is covered by a top cover 194 of the same design as the top cover 94 of the first embodiment. Together the top cover 94 and the inner cup 170 define a second reagent-receiving chamber 196.

In this embodiment, the porous portion 42 of the cartridge C' is provided by the top cover 194, or the fluid-permeable base 158, or both. However, because the top cover is likely to be the most visible of the two to an operator when removing the cartridge after a decontamination cycle, the indicator is preferably printed on, or otherwise affixed to the top cover.

Optionally, as shown in FIG. 5, a stiffener 202, such as an annular ring with a pair of x-shaped cross members, is positioned between the inner cup 170 and the top cover 194 to ensure that the top cover lays flat. Preferably, the stiffener 202 is held in place by frictional or mechanical force.

Of course, for the embodiment of FIG. 5, the lower opener projection 40 of the decontamination system A can be eliminated.

To assemble the cartridge C of the embodiment shown in FIG. 5, the base 158 is first attached to the outer cup 150. The first reagent is then disposed within the outer cup. The inner cup 170 is then placed within the outer cup with the flange 74 of the inner cup resting on the flange 154 of the outer container portion. The second reagent is disposed within the inner cup and the top cover 194 disposed so that it rests on the flange of the inner cup. The top cover, inner cup and outer cup are then sealed together at the flanges of the inner and outer cups. Thus, the first reagent is sealed within the outer cup, while the second reagent is sealed within the inner cup. Other methods of assembling the cups C, C' are also contemplated.

The cartridge C is alternatively constructed according to a variety of different embodiments which serve to keep the dry reagents in separate compartments during transportation and storage, yet allow the reagents to leave the cartridge when dissolved in water, or other suitable solvent, that flows into the cartridge. Where only a single concentrated decontaminant is used, the inner compartment can, of course, be eliminated. In this case, a top cover of the type previously described is sealed directly, around a peripheral edge, to the flange 54, 154 of the outer cup 50, 150.

In a preferred embodiment, the inner and outer cups 50, 150, 70, 170 each contain one of an acid precursor and a persalt. More specifically to the preferred embodiment, the acid precursor is acetylsalicylic acid and the persalt is sodium or other perborates. The two compounds dissolve as water flows through the cartridge. The sodium perborate generates hydrogen peroxide, which, in combination with acetylsalicylic acid as an acetyl donor, forms peracetic acid.

For sterilization, the volume of powdered ingredients is selected relative to the volume of water such that a concentration of approximately 0.2% weight/volume of peracetic acid is achieved in the resultant decontamination solution. Such a concentration is sufficient, under normal circumstances, to maintain a peracetic acid concentration of at least 1500 ppm, and preferably 2000 ppm or better, throughout a sterilization cycle. For disinfection, lower concentrations of peracetic acid may be used.

The sodium perborate solution additionally functions as an inorganic corrosion inhibitor and the salicylic acid as an organic corrosion inhibitor for the decontamination system and for the items to be decontaminated. Optionally, additional corrosion inhibitors, buffers, and a wetting agent are added to these powders. For hard water, in which calcium and magnesium salts may tend to precipitate, a sequestering agent, such as sodium hexametaphosphate, is also included.

It is also contemplated using powdered reagents which react in a common solvent to generate chlorine gas, hydrogen peroxide, hypochlorous acid, hypochlorites, or other strong oxidants which have biocidal effects.

While the cartridge has been described with reference to solid reagents, it should be appreciated that liquid reagents or decontaminants could be contained within the cartridge in addition to or in place of the dry reagents by enclosing the liquid component in a sealed or leak-resistant compartment which is punctured, or otherwise opened, to release the liquid component into the decontaminant solution.

The indicator 44 is one which exhibits a detectable change, such as a visible color change, when mixed with a desired concentration of the decontaminant solution. Particularly preferred are indicators which slowly change color over a period of exposure to the decontaminant solution, rather than changing color rapidly on contact with the decontaminant solution. The indicator may also be temperature dependent, increasing the rate of color change with increased temperatures. Suitable indicators thus act as integrators, the final color change resulting from a combination of the length of exposure to the decontaminant solution, the concentration of the decontaminant in the solution, and the temperature of the decontaminant solution, all of which are known to influence the effectiveness of decontamination. The color change may also be influenced by the flow rate of the decontaminant solution through the porous portion, although in most decontamination systems, the flow rate is maintained at a fairly uniform or reproducible level.

Absence of a color change, or only a marginal color change, indicates that the decontaminant solution was not maintained at a minimum acceptable level for decontamination, while a distinct color change indicates that a sufficient concentration was maintained for a sufficient period of time to ensure sterilization or disinfection of the instruments. optionally, the final color of the indicator after exposure to the decontaminant solution is compared with a standard color chart which identifies an acceptable color range for the level of decontamination desired.

Thus, when the indicator is used in a system such as the decontamination system A of FIGS. 1 and 2, the indicator does not immediately change color when it is exposed to the highly concentrated decontaminant that is initially flushed from the cartridge C. Rather, the indicator progressively changes color as the decontaminant solution recirculates through the cartridge.

The indicator is preferably one which is specific for the decontaminant and is not influenced significantly by other components of the decontaminant solution. For example, in the embodiments of FIGS. 3–5, the indicator responds to peracetic acid and is not significantly influenced by the concentrations of sodium perborate, acetyl salicylic acid, hydrogen peroxide, corrosion inhibitors, buffers, wetting agents, and sequestering agents, and the like, present in the decontaminant solution during a decontamination cycle. Additionally, the indicator is preferably less sensitive to pH than to the decontaminant so that it does not respond significantly to changes in pH of the decontaminant solution. The indicator thus provides a semi-quantitative indication of the integrated level of the decontaminant in the solution over time for determining whether an acceptable level of the decontaminant was present for decontamination.

The indicator is preferably combined with a suitable solvent to form an ink which is printed on, or otherwise impregnated into the porous portion 42. Preferably, the ink binds to the porous material of the porous portion 42 so that the indicator is not extensively leached or washed from the porous portion by the pressure of the decontaminant solution flowing through the cartridge C during the decontamination cycle. Non-woven polypropylene felts, in particular, take printing inks reasonably well and inhibit the ink from being flushed away or seeping extensively throughout the porous portion.

When the decontaminant is peracetic acid to be used for sterilization of medical instruments, the indicator is preferably one which detects a concentration of between about 900 and 1800 ppm, or more of peracetic acid. The concentration of peracetic acid in a sterilization system A of the type shown in FIG. 1 naturally decreases over time so that an initial concentration of over 2000 ppm may drop to around 600–900 ppm during a sterilization cycle, depending on factors such as the level of soil on the instruments. Since the indicator changes color more rapidly at higher concentrations, the overall color change will be a function of the time of exposure and the varying concentration (provided that the temperature of the system is maintained at a fairly constant level). The indicator is selected so that an observable color change occurs when the peracetic acid remains at or above about 900 ppm throughout the cycle, although the indicator could be selected to trip at a different concentration level, for example, for disinfection.

Suitable indicators for peracetic acid include crystal violet, bromocresol green, bromothymol blue, bromothymol green, and methyl purple, although other oxidizable indicators are also contemplated. Crystal violet is a particularly preferred indicator for peracetic acid as it is less sensitive to changes in pH than to peracetic acid concentration. It changes color from purple to light tan or clear during a satisfactory sterilization cycle. Suitable solvents for forming an ink of the indicator include water, polyvinyl alcohol, and cellulosic solvents, such as methyl cellulose, and the like. The cellulosics are particularly effective for binding the ink and indicator to the porous portion 42 of the cartridge C. For crystal violet, a concentration of about 30–190 mg/l crystal violet in the ink is sufficient to provide sufficient initial purple coloration and a final purple or light purple coloration in the case of an unsatisfactory cycle.

The indicator is impregnated on a central region of the top cover 94, 194, preferably during printing of labeling information on the top cover. Alternatively, the indicator is soaked into the top cover and the material dried by air drying or in an oven.

Figure 6:
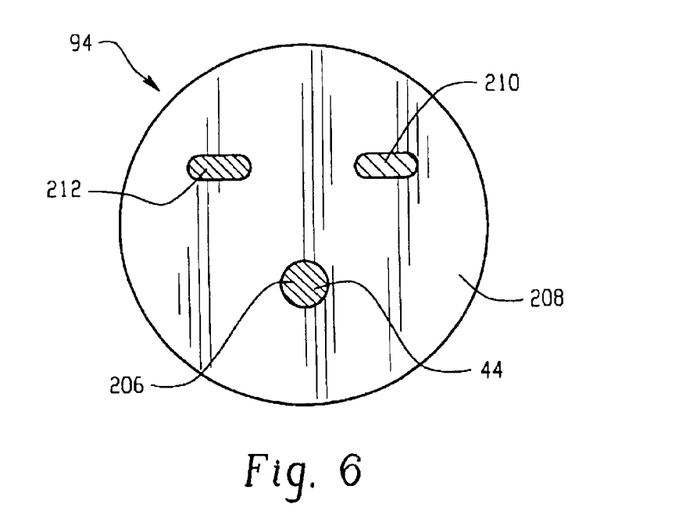
FIG. 6 is a top view of a flow through top of either of the embodiments of the two compartment package of FIGS. 4 and 5 according to one embodiment of the present invention; and, FIGS. 7A and 7B are top views of an alternate embodiment of a flow through top for the two compartment packages of FIGS. 4 and 5 before (FIG. 7A) and after (FIG. 7B) exposure to a successful decontamination cycle.
Figure 7A:
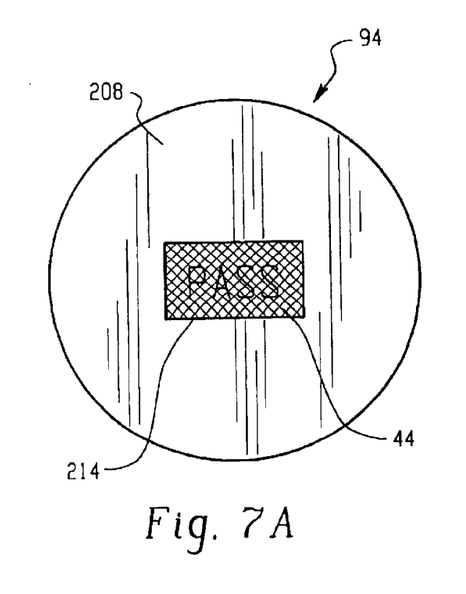
Figure 7B:
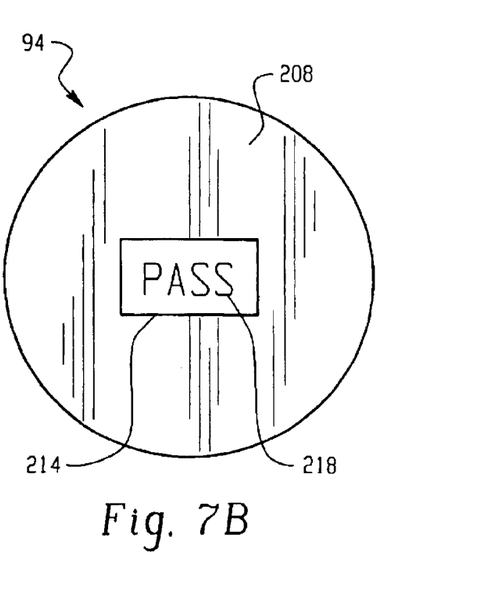

Various configurations for the indicator are possible. Two preferred alternate configurations are shown in FIGS. 6 and 7. In its simplest form, a region 206 of the porous portion 42 is printed or otherwise impregnated with the indicator 44. Preferably, the region 206 forms part of an upper surface 208 of the top cover 94, 194.

With reference to FIG. 6, a region 210 of a reference material is optionally also printed on the top cover 94, 194. The reference material is preferably an ink which is not affected by the decontamination process and is colored to indicate the minimum acceptable coloration of the indicator for a satisfactory decontamination cycle. The reference region may be marked with the word "PASS", or other suitable indication that the color is acceptable. Optionally, a second reference region 212 is impregnated with a second ink which does not change color in the decontamination cycle. The second ink is colored to indicate a coloration of the indicator after an unsatisfactory decontamination cycle, and may be marked with the word "FAIL", or similar.

With reference to FIGS. 7A and 7B, in an alternate embodiment, a region 214 of the indicator 44 is printed over the word "PASS", or similar, which is printed onto the upper surface 208 of the top cover 94 in a stable ink 218. When the indicator decolorizes in a successful decontamination cycle, the word "PASS" becomes clearly visible (FIG. 7B).

In use, the cartridge C is inserted into the well 16 of the decontamination system and items to be sterilized or disinfected placed in the tray 14. Fresh water is circulated through the tray and the well. The concentrated decontaminant forms a decontaminant solution with the water which is recirculated through the tray and the well for a predetermined period, contacting the indicator 44 on the porous region 42 of the top cover 94, 194, or other porous region of the cartridge, in the process. The decontaminant system may then be flushed with water to remove traces of the decontaminant from the decontaminated items. The lid is opened and the operator removes the spent cartridge and records the indication of decontaminant concentration provided by the indicator. If the indicator indicates that insufficient decontaminant was present in the cycle, the items are left in the tray and subjected to a second decontamination cycle with a fresh cartridge C. If the indicator indicates that sufficient decontaminant was present in the cycle, the decontaminated items are removed from the system A and returned to use. The top cover 94, 194 of the cartridge can be removed and stored as a permanent record for the particular cycle.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A single-use package holding a powdered composition which forms a solution of an anti-microbial decontaminant when mixed with water and for releasing the composition when the package is opened or when the composition dissolves and passes through a porous portion of the package, the package comprising:
    a porous portion which is impermeable to the powdered composition but is permeable to water and to the solution; and,
    an indicator on the porous portion which exhibits a detectable change on exposure to the decontaminant in the solution.

2. The package of claim 1, further including:
    a first compartment for receiving a first component of the composition; and,
    a second compartment for receiving a second component of the composition, the porous portion, first compartment, and second compartment configured for forming a fluid flow path for the decontaminant solution through the package.

3. The package of claim 2, wherein the cartridge further includes:
    an outer, first cup including a first peripheral wall with an opening at an end, the first peripheral wall being at least selectively water transmissive;
    an inner, second cup including a second peripheral wall, the second peripheral wall having a detachable base, the first and second cups being configured such that the second peripheral wall abuts and is connected to the first cup adjacent the end of the first peripheral wall;
    a top cover covering the openings in the first and second cups, such that the first compartment is defined in the first cup and the second compartment is defined in the second cup.

4. The package of claim 3, wherein the first cup peripheral wall includes a side and a base, and wherein the base is detachable from the side.

5. The package of claim 2, wherein the decontaminant includes peracetic acid and the first component includes acetylsalicylic acid and the second component includes sodium perborate.

6. The package of claim 2, wherein the package further includes:
    an outer, first cup including a first peripheral wall with an opening at an end, the first peripheral wall being at least selectively water transmissive;
    an inner, second cup including a second peripheral wall, the second peripheral wall having a water permeable portion, the first and second cups being configured such that the second peripheral wall abuts and is connected to the first cup adjacent the end of the first peripheral wall;
    a top cover covering the openings in the first and second cups, such that the first compartment is defined in the first cup and the second compartment is defined in the second cup.

7. The package of claim 6, wherein the first peripheral wall includes a region which is formed from a first material which is impermeable to the first component but is permeable to water and to solutions containing dissolved components.

8. The package of claim 6, wherein the second peripheral wall includes a region which is formed from a second material which is impermeable to the first and second components but is permeable to water and to solutions containing dissolved components.

9. The package of claim 8, wherein the second peripheral wall defines a hemisphere and is formed from the second material.

10. The package of claim 1, wherein the porous portion is formed from a material selected from the group consisting of non-woven polypropylene web, woven polypropylene, woven polyethylene, non-woven polyethylene, nylon, rayon, rigid porous media, porous plastic, mesh, and combinations thereof.

11. The package of claim 1, wherein the indicator includes an oxidizable species which changes color on prolonged contact with the solution.

12. The package of claim 1 wherein the indicator is specific for the decontaminant.

13. The package of claim 1, wherein the indicator is less sensitive to pH than to the decontaminant.

14. The package of claim 1, wherein the indicator is impregnated into the porous portion in the form of an ink.

15. The package of claim 1, wherein the decontaminant is peracetic acid and the indicator provides a detectable color change when the peracetic acid is at a concentration of about 900 ppm or above for a preselected period of time.

16. The package of claim 1, wherein the decontaminant is peracetic acid and the indicator is selected from the group consisting of crystal violet, bromocresol green, bromothymol blue, bromothymol green, methyl purple, and combinations thereof.

17. The package of claim 16, wherein the indicator includes crystal violet.

18. A single use package for holding a dry composition which forms an anti-microbial solution when mixed with water, the package comprising:
   a side wall;
   a bottom wall across a lower portion of the sidewall;
   a top cover across an upper portion of the side wall, the top cover defining a porous portion which is impermeable to the dry composition but is permeable to water and to the solution; and
   an indicator on the top cover which exhibits a detectable change on exposure to the anti-microbial solution.

19. A package for holding an anti-microbial concentrate which forms an anti-microbial solution when mixed with water, the package releasing anti-microbial concentrate at a selected time in an anti-microbial cycle, the package comprising:
   a porous portion which is impermeable to the anti-microbial concentrate but is permeable to water and to the solution; and
   an indicator on the porous portion which exhibits a detectable color change when exposed to a preselected minimum concentration of the decontaminant for a preselected minimum period of time to indicate the formulation of an anti-microbial solution capable of effecting anti-microbial decontamination.

20. An anti-microbial system comprising:
   a well for receiving a single use package, the package including:
      at least one cup which holds an anti-microbial concentrate, the cup including an inlet,
      a porous portion affixed to the cup inlet which is permeable to water and to an anti-microbial solution formed from the anti-microbial concentrate and the water, and
      an indicator on the porous portion which exhibits a detectable change on exposure to a decontaminant in the solution;
   a source of water connected with the well for mixing with the anti-microbial concentrate and forming the anti-microbial solution;
   a microbial decontamination chamber connected with the well for receiving the anti-microbial solution, the well, the porous region, and the chamber forming a recirculating fluid flow path for the anti-microbial solution, whereby the recirculating anti-microbial solution passes over the indicator.

21. A package for releasing an anti-microbial composition into a flowing liquid, the package comprising:
   a side wall having a first opening at a first end and a second opening at a second end such that the liquid flows through the first opening into the package and out through the second opening;
   a layer of porous material spanning one of the first and second openings such that the liquid flows through the porous material layer;
   an anti-microbial source disposed within the package for releasing the anti-microbial composition into the flowing liquid to form an anti-microbial solution;
   an indicator on the porous material layer which changes color in response to contact with the anti-microbial solution, a degree of color change varying in accordance with (i) a concentration of an anti-microbial agent in the solution contacting the indicator, and (ii) a duration that the solution contacts the indicator such that the degree of color change of the indicator is indicative of duration of contact and the concentration of the anti-microbial agent in the contacting solution.

22. A method comprising:
   flowing water through a cartridge containing a composition to form a decontaminant solution from the composition and the water, the cartridge including a porous region impregnated with an indicator, the indicator exhibiting a preselected detectable change when contacted with a decontaminant solution and at a concentration of a decontaminant in the solution sufficient to effect decontamination of items;
   circulating the decontaminant solution in a fluid flow path comprising a microbial decontamination chamber, in which the items to be decontaminated are positioned, and the porous region;
   examining the indicator for the detectable change.

23. An anti-microbial system comprising:
   a well for receiving a single use package, the package including:
      at least one cup which holds an anti-microbial source for forming an antimicrobial solution when mixed with water,
      a porous portion connected to the cup and being permeable to water and to an anti-microbial solution formed from the anti-microbial source and the water, and
      an indicator carried on the porous portion which exhibits a detectable change on exposure to a decontaminant in the anti-microbial solution;
   a source of water connected with an inlet to the well for mixing with the anti-microbial source and forming the anti-microbial solution;
   a microbial decontamination chamber for receiving the anti-microbial solution from an outlet from the well;
   a fluid line connecting the chamber with the well outlet;
   the well, the fluid line, and the chamber forming a recirculating fluid flow path for the anti-microbial solution through the porous region, whereby the recirculating anti-microbial solution passes over the indicator.

* * * * *